United States Patent
Duprat et al.

(10) Patent No.: US 7,175,639 B2
(45) Date of Patent: Feb. 13, 2007

(54) CUTTER BLADE ASSEMBLY FOR A MICROKERATOME

(75) Inventors: Alain Duprat, Antony (FR); Jean-Luc Aufaure, Souvigny (FR)

(73) Assignee: Moria SA, Antony (FR)

( * ) Notice: Subject to any disclaimer, the term of this patent is extended or adjusted under 35 U.S.C. 154(b) by 516 days.

(21) Appl. No.: 10/475,103

(22) PCT Filed: Apr. 15, 2002

(86) PCT No.: PCT/FR02/01296

§ 371 (c)(1),
(2), (4) Date: Oct. 17, 2003

(87) PCT Pub. No.: WO02/083042

PCT Pub. Date: Oct. 24, 2002

(65) Prior Publication Data

US 2005/0075658 A1  Apr. 7, 2005

(30) Foreign Application Priority Data

Apr. 18, 2001 (FR) .................................. 01 05228

(51) Int. Cl.
*A61F 9/00* (2006.01)

(52) U.S. Cl. ..................................................... 606/166

(58) Field of Classification Search ................. 606/166, 606/167, 178, 177, 172; 600/452
See application file for complete search history.

(56) References Cited

U.S. PATENT DOCUMENTS

| 5,980,543 A | 11/1999 | Barraquer et al. |
| 6,540,760 B2 * | 4/2003 | Austring et al. ............ 606/166 |
| 6,923,821 B2 * | 8/2005 | Wortrich ..................... 606/166 |

FOREIGN PATENT DOCUMENTS

| EP | 1 027 873 | 8/2000 |
| FR | 2 751 206 | 1/1998 |
| WO | 99/26568 | 6/1999 |

* cited by examiner

*Primary Examiner*—Kevin T. Truong
(74) *Attorney, Agent, or Firm*—Young & Thompson

(57) ABSTRACT

A cutting blade assembly for microkeratome includes a blade (8) with a rectilinear cutting edge (9), the blade being integral with a support (10) with substantially constant profile (11) along one longitudinal dimension parallel to the cutting edge (9) and delimited by an outer surface (12) having a notch (14) substantially orthogonal to the cutting edge (9) of the blade (8), wherein the outer surface (12) has a clearance (15, 17) parallel to the cutting edge of the blade extending from one end (10a) of the support up to a specific distance of the notch (14).

4 Claims, 1 Drawing Sheet

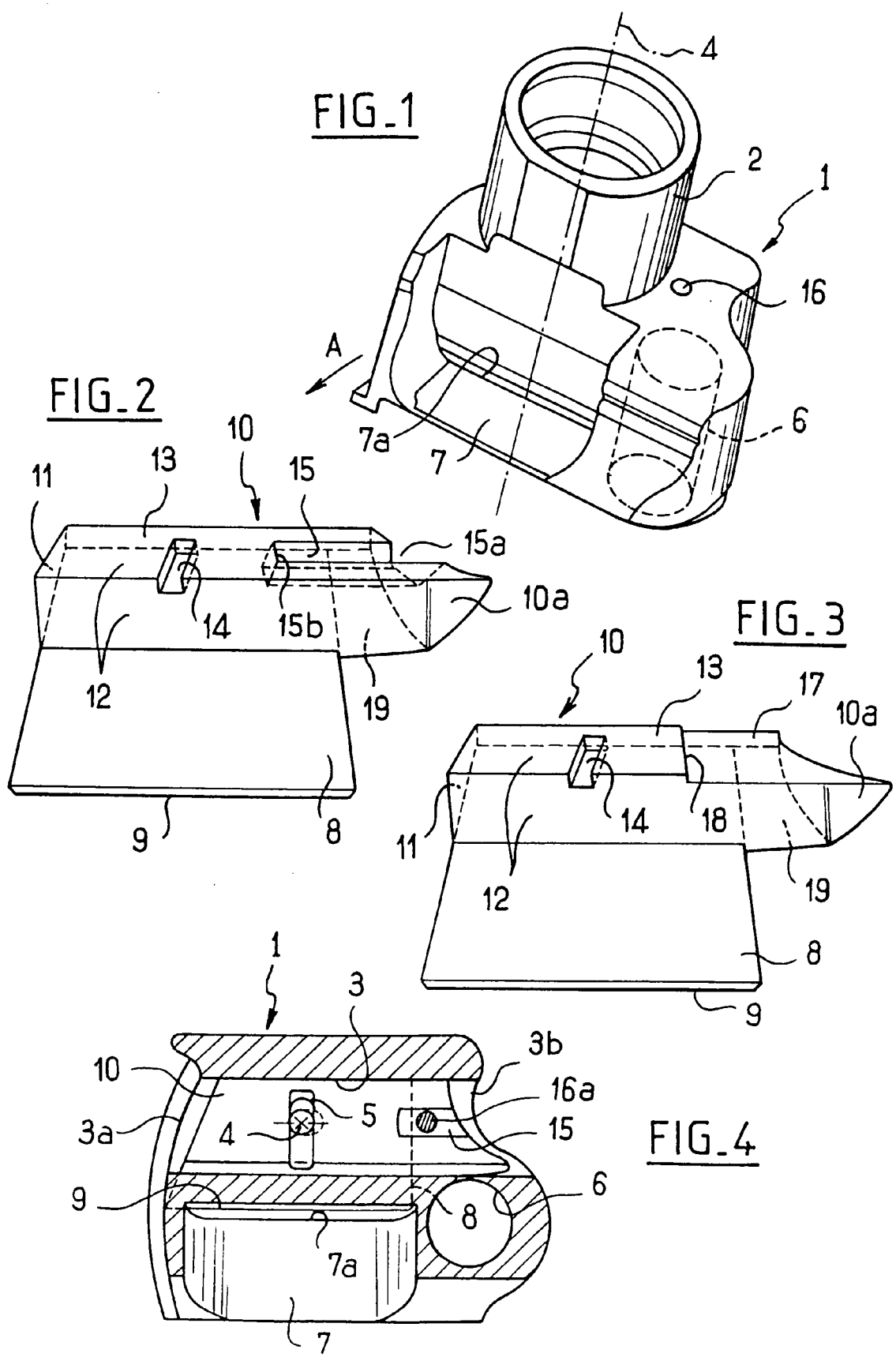

CUTTER BLADE ASSEMBLY FOR A MICROKERATOME

Surgical instruments for refractive ophthalmology include microkeratomes, in which a cutter head has a cutter blade mounted to slide in a guide housing and driven in said housing with linear reciprocating motion by means of a drive finger co-operating with the blade (or a support secured thereto), the drive finger generally being mounted to rotate eccentrically at the end of a drive shaft that extends perpendicularly to the direction of blade motion.

BACKGROUND OF THE INVENTION

The drive shaft is situated at the end of a motor unit, and the cutter head of the keratome is releasably fixed thereto. The finger projects into the sliding housing for the blade so as to reach a coupling groove of the blade (or its support) and be received therein.

Perpendicularly to the motion of the blade, the housing provided in the head possesses a section that is substantially identical to the section of the blade and support assembly which slides therein, ignoring operating clearance. This housing passes through the head, and the blade is slid into the housing through one of its ends prior to the head being assembled to the motor unit. It is only after the head has been assembled on the motor unit that the drive finger holds the blade in said housing by penetrating into the groove.

It is a drawback to need to take care to keep the blade present inside the housing of the head until it has been assembled onto the motor unit, particularly since it is necessary to manipulate the head while it is being assembled, and it is at this time that the blade might escape from its housing if care is not taken.

It is also a drawback to have no control over the position of the blade inside the housing of the head at the time it is being mounted on the motor unit. The volume swept by the drive finger while it is rotating is relatively small (the reciprocating stroke of the blade has a peak-to-peak amplitude of about 1 millimeter), such that the groove in the blade might not intersect this volume, and as a result when the finger is put into rotation co-operation between the finger and the groove does not occur.

OBJECTS AND SUMMARY OF THE INVENTION

The assembly of the invention seeks to remedy at least some of these drawbacks and provides the surgeon with means for reliably preparing each new blade that is to be used for each operation.

To this end, the invention provides a cutter blade assembly for a microkeratome, the assembly comprising a blade having a rectilinear cutting edge and being secured to a support of profile that is substantially constant along a longitudinal dimension parallel to the cutting edge and that is defined by an outside surface including a notch substantially orthogonal to the cutting edge of the blade, wherein said outside surface possesses a setback parallel to the cutting edge, extending from one end of the support to a determined distance from the notch.

This setback makes it possible to put the projecting element into place in the housing where it can co-operate with the end of the setback firstly to prevent the blade assembly, which is inserted into one end of the housing of the cutter head, from escaping from the housing through its opposite end, and secondly to stop the assembly (blade plus support) in a position such that the groove that is to co-operate with the drive finger necessarily lies in the volume swept by the finger during rotation of the drive shaft.

In a first embodiment, the setback is formed by a groove open to the end of the support. In which case, the obstacle put into place in the guide housing for the cutter blade assembly is constituted by the end of a cylindrical peg. Co-operation between the longitudinal groove and the peg may provide additional guidance to the cutter blade assembly during its reciprocating motion.

In another embodiment of the invention, the setback is formed by a step in the outside surface of the support having one end beside the notch in the form of a slope connecting the outside surface to the step. This connection slope performs the same functions as the end of the groove in the preceding embodiment, the abutment co-operating with said slope being of any suitable shape.

Insofar as the abutment secured to the cutter head and projecting into the sliding housing in which the blade assembly is mounted against a spring tending to push it into the inside of the housing, this abutment also serves as a member for pressing the cutter blade assembly against a reference surface of the housing, thereby improving its stability in operation.

Finally, the blade support possesses an end that projects beyond the cutter blade and that is of section that tapers progressively. Because of its truncated pyramid shape, this pointed end helps put the cutter blade assembly into place in the housing of the head.

BRIEF DESCRIPTION OF THE DRAWINGS

Other characteristics and advantages appear from the description given below of two embodiments of the cutter blade assembly of the invention.

Reference is made to the accompanying drawing, in which:

FIG. 1 is an outside view of a prior art cutter head used in a keratome for surgery of the cornea;

FIGS. 2 and 3 are two perspective views of two cutter blade assemblies of the invention; and FIG. 4 is a section view of a cutter head fitted with the blade assembly shown in FIG. 2.

MORE DETAILED DESCRIPTION

The cutter head shown in FIG. 1 consists of a one-piece body 1 of known type which can be screwed, or more generally coupled, to the end of a motor member (not shown) by means of a fixing socket 2. In addition to complementary connection means for fixing to the head 1, this motor member presents at its connection end a shaft for driving a cutter blade device which is slidably mounted in a housing 3 of the head 1, as seen in FIG. 4. The axis of the drive shaft is referenced 4 in FIGS. 1 and 4. At its end, the shaft possesses a drive finger 5 that is eccentric relative to the axis 4.

In the example shown, the head presents a cylindrical bore 6 enabling it to be mounted to pivot about the axis of said bore on a pivot belonging to the ring for fixing to the eye on which an operation is to be performed. During the operation, the head 1 pivots about the pivot in the direction referenced A in FIG. 1. At the front of the housing, still in conventional manner, the head possesses a cornea-flattening plate 7, with the cutting edge of the cutter blade being situated behind and slightly below the rear edge 7a of the plate.

The housing 3 is a housing having a longitudinal direction orthogonal to the axis 4 and having a profile that is constant, extending right through the body 1 of the cutter head. The cutter device, which the housing is suitable for receiving, is shown in FIGS. 2 and 3. In FIG. 2 as in FIG. 3, it can be seen that the cutter blade device comprises a blade proper 8 with a rectilinear cutting edge 9 secured to a support 10 that is elongate in a longitudinal direction substantially parallel to the rectilinear cutting edge 9. The section of the support 10 is substantially constant (see its end 11 in the figures) and the support is fixed to the blade in conventional manner, e.g. by means of a bottom stud engaged in a corresponding opening formed in the rear of the blade and not shown in the drawings.

The support 10 has an outside surface 12 which is shown as having a top face 13 in this case. Although the blade is disposed in conventional manner inside the head 1 so as to slope downwards and forwards, the face 13 in the examples shown extends perpendicularly to the axis 4. This face 13 presents a groove 14 that is substantially orthogonal to the cutting edge 9 of the blade, this groove being for receiving the drive finger 5 of the motor unit. The top surface 13 shown in FIG. 2 has a second groove 15 that opens out at 15a to the end of the support and that possesses an end 15b beside the groove 14 and situated at a determined distance from the groove.

A peg 16 is forced into the head 1 so that its bottom end 16a projects into the housing 3 towards the top face 13 of the support 10. The cutter blade assembly is inserted into the housing 3 from its end 3a. This insertion is performed prior to the head being coupled to the motor unit. When the assembly 8, 10 is inserted into the housing 3, it slides towards the opposite end 3b thereof until it is stopped by the end 16a of the peg 16 coming into abutment against the end 15b of the groove 15. Once this contact is achieved, the groove 14 is in a position such that the drive finger 5 will necessarily engage in the groove 14 after making not more than half a turn about the axis 4 once the head has been mounted on the motor unit. Nevertheless, it should be observed that once the finger 5 has been received in the groove 14, it is important to ensure that the end 15b of the groove 15 does not strike against the end 16a of the peg 16 during the reciprocating motion cycle performed by the cutter blade assembly. For this purpose, a groove 14 is provided whose flanks flare slightly so that when the finger 5 is at its closest to the peg 16, the end 15b of the groove 15 does not touch said peg. More precisely, it is appropriate for the flank of the groove 14 situated remote from the end 15b of the groove 15 to slope downwards, with the width of the groove 15 being greater at the top of the groove than the diameter of the finger 5. The other flank of the groove 14 should be perpendicular, being closer to the end 15b than the shortest distance between the finger 5 and the peg 16.

The variant of the cutter blade assembly of the invention shown in FIG. 3 differs from that shown in FIG. 2 only by having a step 17 instead of and replacing the groove 15. This step terminates at a slope or riser 18 where it joins the face 13. The position of this slope 18 relative to the groove 14 is, and for the same reasons, identical to the position of the end 15b of the groove 15.

The peg 16 may be mounted in the head 1 against a spring which tends to cause it to project into the housing 3. The peg whose end may be rounded or which may co-operate with a bottom of the groove 15 that slopes or with a step 17 that slopes likewise rising towards the groove 14 can be raised slightly by the cutter blade assembly being inserted in the housing 3 and can maintain a thrust force urging said assembly against the bottom surface of the housing 3. This bearing pressure can improve the stability of the blade during its reciprocating motion.

In FIGS. 2 and 3, it should be observed that the support 10 has one end projecting beyond the blade 8. This projection constitutes an end for inserting and guiding the blade assembly into the housing 3, and in order to improve insertion, it can be seen that the projecting end of the support 10 is pointed in shape at 10a, corresponding substantially to the end of a tetrahedron. It should be observed that the tip of the tetrahedron is situated a small way inside the transverse profile of the support 10. Finally, it should be observed that there is an inside surface 19 between the base of the tip 10a and the portion of the support 10 directly overlying the blade 8, which surface connects the tip 10a to the bottom surface of the blade 8. This sloping surface improves initial guidance of the cutter blade assembly into the opening of the housing 3.

The invention claimed is:

1. A cutter blade assembly for a microkeratome, the assembly comprising a blade (8) having a rectilinear cutting edge (9) and a blade support (10) of profile (11) that is substantially constant along a longitudinal dimension parallel to the cutting edge (9) and that is defined by an outside surface (12) including a notch (14) substantially orthogonal to the cutting edge (9) of the blade (8), wherein said outside surface (12) possesses a setback (15, 17) parallel to the cutting edge, extending from one end (10a) of the support to a limiting wall transversely located between said one end and said notch.

2. An assembly according to claim 1, wherein the setback is formed by a groove (15) managed in said outside surface and open to said one end (10a) of the support (10).

3. An assembly according to claim 1, wherein the setback is formed by a step (17) in the outside surface (12) of the support having one end (18) beside the notch (14) in the form of a slope connecting the outside surface to the step.

4. A cutter blade assembly according to claim 1, wherein the support (10) possesses an end (10a) projecting beyond the cutter blade (8) and of section that tapers progressively.

* * * * *